United States Patent
Divi et al.

(10) Patent No.: US 8,389,790 B2
(45) Date of Patent: Mar. 5, 2013

(54) PROCESS FOR ISOMERISATION OF LYCOPENE IN THE PRESENCE OF THIOUREA

(75) Inventors: Murali Krishna Prasad Divi, Hyderabad (IN); Gundu Rao Padakandla, Hyderabad (IN); Nageswara Rao Bolneni, Hyderabad (IN); Ramesh Babu Kodali, Hyderabad (IN)

(73) Assignee: Divi's Laboratories, Ltd. (IN)

( * ) Notice: Subject to any disclaimer, the term of this patent is extended or adjusted under 35 U.S.C. 154(b) by 153 days.

(21) Appl. No.: 13/081,087

(22) Filed: Apr. 6, 2011

(65) Prior Publication Data

US 2012/0197055 A1 Aug. 2, 2012

(30) Foreign Application Priority Data

Feb. 1, 2011 (IN) .............................. 297/CHE/2011

(51) Int. Cl.
*C07C 5/23* (2006.01)
*C07C 5/25* (2006.01)

(52) U.S. Cl. ...................... 585/664; 585/600

(58) Field of Classification Search ............ 585/664
See application file for complete search history.

(56) References Cited

U.S. PATENT DOCUMENTS 2,454,387 A * 11/1948 Howland et al. ............... 562/591
2,548,687 A * 4/1951 Spatz ............................ 562/591
7,126,036 B2 10/2006 Wegner et al.

FOREIGN PATENT DOCUMENTS

GB 2207915 A 2/1989

OTHER PUBLICATIONS

The United States Pharmacopeial Convention, Lycopene Preparation, Revision Bulletin, Official Mar. 1, 2009.
Robert K. Muller, et al. (E/Z/-Isomeric Carotenes, Pure & Appl. Chem. vol. 69, No. 10. pp. 2-39-2046, 1997.
Ase Eidem, et al. Bacterial Carotenoids, XLVIII, Total Syntheses of Carotenes of the 1,2-Dihydro Series, Acta Chem. Scand. B 29 (1975) No. 10, Organic Chemistry Laboratories, Norwegian Institute of Technology, University of Trondheim, N-7034 Trondheim, Normay.
Urs Hengartner, et al. Synthesis, Isolation, and NMR-Spectroscopic Characterization of Fourteen(Z)-Isomers of Lycopene and of some Acetylenic Didehydro-and Tetradehydrolycopenes, Helvetica Chimica Acta—vol. 75(1992).
Chemical reviews 2003, vol. 103, No. 7.
Von Albrecht Zumbrumm, et al., HPLC von Carotinen mit—Endgruppen und (Z)-Konfiguration an terminalen konjugierten Dopppelbindungen; Isolierung von (5Z)-Lycopin aus Tomaten, Helvetica Chimica Acta—vol. 68 (1985).
Robert K. Muller, et al., (E/z)-Isomeric carotenes, Pure & Appl. Chem. vol. 69, No. 10, pp. 2039-2046, 1997.
Clinton, et al, cis-trans Lycopene Isomers, Carotenoids, and Retinol in the Human Prostate, Cancer Epidemiology, Biomarkeers & Prevention, vol. 5, 823-833, Oct. 1996.
P.S. Manchand, et al. Carotenoids and Related Compounds, Part XI. Syntheses of Carotene and Carotene, J. chem. soc. 2019, 1965.
Shaleen K. Lee, et al. Urea and thiourea Inclusion complexes ofconjugated Polyenes: Polarized Fluorescence Excitation and Resonance Raman Studies, Mol. Cryst. Liq. Cryst. 1992, vol. 211, pp. 147-156.
European Search Report dated May 22, 2012.

* cited by examiner

*Primary Examiner* — In Suk Bullock
*Assistant Examiner* — Philip Louie
(74) *Attorney, Agent, or Firm* — Caesar, Rivise, Bernstein, Cohen & Pokotilow, Ltd.

(57) ABSTRACT

The present invention relates to isomerization of Z-lycopene in mixtures of isomers to mixtures enriched with all E-lycopene.

4 Claims, No Drawings

PROCESS FOR ISOMERISATION OF LYCOPENE IN THE PRESENCE OF THIOUREA

CROSS-REFERENCE TO RELATED APPLICATIONS

This application claims priority from India Application Serial No. 297/CHE/2011, filed on Feb. 1, 2011, entitled PROCESS FOR ISOMERISATION OF LYCOPENE IN THE PRESENCE OF THIOUREA which application is assigned to the same assignee as this application and whose disclosure is incorporated by reference herein.

FIELD OF INVENTION

The present invention relates to an improved process for isomerization of Z-lycopene to E-lycopene substantially, wherein isomerization takes place in the presence of a catalytic amount of thiourea.

BACKGROUND OF THE INVENTION

Lycopene is a carotenoid substance naturally occurring in tomatoes and many other plant and microbial sources, as a mixture of geometrical isomers. It is an acyclic molecule of formula $C_{40}H_{56}$, with 11 conjugated and 2 isolated double bonds. (Carotenoids, G. Britton, S. Liaaen-Jensen and H. Pfander, Birkhauser Verlag, Basel, Several volumes, 1995 to 2004). Theoretically there can be many isomers possible. Some of them definitely occur naturally, although it is very difficult to distinguish them from each other by simple spectroscopic methods. For example, the (5-Z) and the all-E isomers have identical UV-Vis spectrum and can be identified only when resolved by RP-HPLC. Eight (mono-Z) isomers were obtained by controlled stereospecific synthesis and six from isomerization mixtures. Four (di-Z) isomers and one (tetra-Z) isomer have also been reported. (Hengartner et al, *Helv. Chim. Acta,* 75, 1848, 1992). Lycopene from natural sources has been used as a coloring ingredient in foods. It has also been recommended as a useful anti-oxidant. There are no specific reports in the literature on the relative biological activities of the isomers of lycopene. Tomatoes are the major source of lycopene in human nutrition and are known to contain 71 to 90% of all-E-lycopene (all-trans) and 9 to 21% of Z-isomers (cis), mainly the 5-Z-isomer (Zumbrum et al, *Helv. Chim. Acta,* 68, 1540, 1985), depending on the source, season etc. Surprisingly in humans all-E lycopene accounted for only 12 to 21% whereas the Z-isomers accounted for 79 to 88% in benign or malignant prostate tissue. (Clinton et al., Cancer *Epidemiol. Biomarkers Prev.,* 5, 823, 1996). This means the human body is converting much of the all-E isomer to Z-isomers which may be influencing malignant growth. In beta-carotenes and retinoids the all-E isomers are definitely known to be more active than the Z-isomers. It is thus considered preferable to use all-E lycopene and avoid Z-lycopenes for human consumption. The USP-NF monograph on lycopene is a mixture of all-E lycopene containing up to 23% of 5-Z lycopene, the major isomer in natural lycopene. Synthetic lycopene is better controlled in terms of isomers compared to natural sources. Even so, it is known that the (5-Z)-isomer predominates under certain conditions. A stereospecific synthesis of all-E lycopene suppressing the formation of Z-isomers would be very expensive. A process which enables isomerization of the Z-isomers to all-E isomer is attractive when a synthetic route for lycopene is adopted for its large scale production.

Isomerization of carotenoid compounds is known. Most studies deal with mechanics and mechanisms of photoisomerization and some with enzyme induced isomerizations. (See Dugave and Demange, *Chem. Rev.,* 103, 2481, 2003). Mueller et al. (*Pure & Appl. Chem.* 69, 2039, 1997) have reviewed the topic and reported that in solution (E/Z)-isomerization of carotenoids is promoted by heat, light, active surfaces and catalytic amounts of acids or iodine. It is believed that the Wittig and Horner condensation steps in the synthesis of carotenoids lead to isomeric mixtures and isomerization could be effected thermally in non-polar solvents. However, the focus in this publication was on preparation of Z-isomers in pure form by isomerization of the all-E lycopene. U.S. Pat. No. 7,126,036 discloses a process of thermal isomerization of lycopene. The process essentially consists of first dissolving the mixture of all-E and Z-isomers in a non-polar solvent dichloromethane followed by addition of methanol, distilling off azeotropically dichloromethane to obtain a suspension in methanol which is then subjected to thermal isomerization by refluxing in methanol or under autogenous pressure raising the temperature to about 95° C. The yields of the enriched all-E isomer or the extent of isomerization did not improve with the autogenous pressure. Although the inventors claimed enrichment of the all-E isomer in mixtures of any proportion of the two isomers, all the examples indicate that the starting mixture consisted of 53% of all-E isomer. The Z-isomer content in the starting mixture is reported as 18%. The inventors achieved enrichment to about 76 to 87% of all-E isomer at the end of the process. The content of the Z-isomer in the enriched mixtures have not been revealed. The extent of isomerization of the Z-isomer to the all-E isomer is thus not clear. Example 7, without thermal isomerization, also achieved enrichment to 75% of all-E isomer in the crystallized sample indicating that solubility and crystallization steps also contributed to a large extent in the process.

We attempted to repeat the thermal isomerization process as described in the U.S. Pat. No. 7,126,036. We used samples containing about 56% of all-E and about 43% of Z-isomers (predominantly 5-Z-isomer) and also containing about 20 to 22% all-E and about 62 to 72% of Z-isomers. Divis product that is routinely obtained from the manufacturing process has this latter composition. The results obtained from these experiments are summarized in the Table 1 below.

TABLE 1

| Input material | | Reaction | Composition of output material | | Notes |
|---|---|---|---|---|---|
| All-E (%) | Z- (%) | time (hrs) | All-E (%) | Z- (%) | |
| 56.5 | 43.5 | 15 | 73.4 | 26.5 | a |
| 56.5 | 43.5 | 30 | 74.8 | 25.2 | a |
| 56.5 | 43.5 | Isolated solid | 74.1 | 25.9 | a |
| 22.7 | 72.5 | 16 | 20.8 | 73.1 | b |
| 22.7 | 72.5 | 44 | 21.2 | 72.1 | b |
| 22.7 | 72.5 | Isolated solid | 24.4 | 74.8 | b |
| 28.1 | 62.4 | 6 | 48.7 | 43.5 | $c_1$ |
| 28.1 | 62.4 | 12 | 33.8 | 62.1 | $c_2$ |
| 28.2 | 64.2 | 15 | 27.5 | 72.5 | d |
| 28.2 | 64.2 | 30 | 30.7 | 69.3 | d |

Notes:
a: 43 g input;
b: 25 g input, yield ~22 g;
$c_1$: 20 g input, 120° C., 7 bar pressure;
$c_2$: 20 g input, 95° C., 1.8 bar pressure;
d: 43 kg input (pilot scale).

From the results it can be seen that thermal isomerization of lycopene does not take place when the Z-isomer content is higher than that of all-E isomer. Best result is seen at high temperature and pressure with some enrichment but not satisfying the USP-NF specification of less than 23% of the Z-isomer content. Since lycopene is used as additive to foods and medicaments it was felt desirable to avoid chlorinated hydrocarbon solvents in the final steps of synthesis.

We also attempted to use other solvents in the thermal isomerization experiments. The results are shown in Table 2 below:

TABLE 2

Thermal isomerization in different solvents:

| Lycopene | | | | Output lycopene | |
|---|---|---|---|---|---|
| all-E (% A) | Z- (% A) | Solvent | Yield | all-E (% A) | Z- (% A) |
| 30.4 | 57.5 | Toluene | Decomp. | — | — |
| 30.4 | 57.5 | Toluene with Iodine (0.01 g) | Decomp. | — | — |
| 32.6 | 54.7 | IPA | 80% | 43.1 | 52.9 |
| 32.6 | 54.7 | Pet. ether | 80% | 37.2 | 53.1 |
| 32.6 | 54.7 | Water | 84% | 50.9 | 45.0 |
| 30.4 | 57.5 | n-Hexane | 70% | 46.2 | 49.3 |
| 32.6 | 54.7 | n-Heptane | 80% | 36.8 | 54.0 |

It can be seen that the best result was obtained in water as medium in respect of both yield and extent of isomerization. However this was still much below requirement.

There is a need for an improved process of isomerization of Z-isomers present in the synthetic lycopene used as additive in foods or as antioxidant in medicaments. In particular, it was necessary to isomerize mixtures containing low levels of all-E isomer (less than 50%) and high levels of Z-isomers as obtained in commercial manufacture and to avoid halohydrocarbon solvents in the process.

SUMMARY OF THE INVENTION

The present invention reveals an improved process of isomerization of Z-isomers present in the lycopene product obtained during synthesis, wherein the all-E isomer content is less than 50% and the content of Z-isomers is more than the all-E-isomer. The process is carried out in the presence of thiourea as a catalyst in a polar solvent without pressure and halohydrocarbon solvents. The resulting product has a content of all-E isomer greater than 80% with less than 10% of Z-isomers.

DETAILED DESCRIPTION OF THE INVENTION

Lycopene is obtained by synthesis by any of the processes described in the literature (e.g. *Helv. Chim. Acta* 75, 1848, 1992; *Acta Chemica Scandinavica B* 29, 1015, 1975; *J. Chem. Soc.* 2019, 1965). Lycopene is a symmetrical molecule and the strategy that is usually adopted consists of condensation of two molecules of the C-15 intermediate with one molecule of the C-10 intermediate. The C-15 intermediate is usually the Wittig salt of 3,7,11-trimethyl-1,4,6,10-tetraene-dodecan-3-ol and the C-10 intermediate is usually 3,7-dimethyl-2,4,6-octatetraene-1,8-dialdehyde (often called 'dial'). The reaction is generally carried out in a non-polar solvent like dichloromethane or hexane in presence of a strong base like sodium methoxide or potassium t-butoxide. The product may be isolated as a crude solid on work up or further purified by suitable recrystallisation procedures. For our experiments we used the crude solid. The crude lycopene product or the purified material contains a high proportion of Z-isomers ranging from about 40 to about 65% and the all-E isomer in the crude may be as low as about 25%.

An exhaustive search of literature revealed no attempts to preferentially increase the all-E isomeric content of isomeric mixtures of polyenes similar to carotenoids. We could find only a few references to isomerization of olefins in presence of some 'catalysts' like acids, sodium bisulfate, ammonium bromide, ammonium persulfate, potassium bromate, urea, thiourea etc., applied particularly to isomerization of maleic acid (cis-) to fumaric acid (trans-). (See GB2207915 and references cited therein). We attempted to isomerize lycopene product obtained by synthesis as outlined above with several of the 'catalysts' used in the reported isomerization of maleic acid to fumaric acid. Although most of them did not work, we were pleasantly surprised to find addition of thiourea induced satisfactory isomerization of 'lycopene' mixtures to enriched all-E lycopene.

We studied the effect of the input quantity of thiourea on yield and extent of isomerization. Table 3 below summarizes typical results obtained.

TABLE 3

Effect of thiourea on isomerization of lycopene

| Lycopene | | | | Output lycopene | |
|---|---|---|---|---|---|
| Input (g) | all-E (% A) | Z-(% A) | Thiourea input (g) | Yield (g) | all-E (% A) | Z-(% A) |
| 1.0 | 39.5 | 48.2 | 0.0 | 0.7 | 43.1 | 52.9 |
| 1.0 | 38.7 | 49.1 | 0.01 | 0.5 | 47.7 | 43.8 |
| 1.0 | 38.7 | 49.1 | 0.05 | 0.45 | 74.3 | 20.4 |
| 1.0 | 39.5 | 48.2 | 0.10 | 0.78 | 75.7 | 20.9 |
| 1.0 | 39.5 | 48.2 | 0.25 | 0.78 | 88.9 | 6.7 |
| 1.0 | 39.5 | 48.2 | 0.5 | 0.82 | 84.4 | 12.1 |
| 1.0 | 39.5 | 48.2 | 0.5 | 0.80 | 84.5 | 12.7 |
| 1.0 | 39.5 | 48.2 | 1.0 | 0.82 | 83.1 | 14.5 |

It can be seen that thiourea input should be about 25% of the input lycopene to achieve optimal isomerization and yield.

The crude lycopene as obtained by synthesis is suspended in a polar solvent like methanol or isopropanol, solid thiourea is added, the mixture heated to reflux temperature at atmospheric pressure and maintained for several hours. The isomerization process is monitored by in process checks. When the desired proportion of the all-E and Z-isomers is achieved, the reaction is stopped and suitable work up is adopted to recover and purify the lycopene.

The isomerisation process is monitored by HPLC analysis using YMC-Carotenoid (250×4.6 mm) 5 µm and YMC-Carotenoid (250×4.6 mm) 3 µm dual columns connected in series, detection at 472 nm at flow rate of 1.0 ml/minute, tertiary butyl methyl ether:methanol:tetrahydrofuran as mobile phase at a ratio of 784:665:74, injection volume: 10 micro liter of sample solution and run time of 60 minutes.

EXAMPLES

The following examples are for illustration purposes only and do not limit the invention in any way. The reagents and solvents mentioned in examples may be replaced by other reagents and solvents known to those skilled in the art.

Example 1

Lycopene (11.6 g, all E-content 29%) was charged to a 250 ml three necked round bottomed flask containing 2-propanol (75 ml). To the resulting suspension, 2.9 g of thiourea was added and heated to maintain a temperature of 90-95° C. for 15 hrs. The solvent was distilled at reduced pressure at 55-60° C. To the residue, methanol (50 ml) was added, stirred at 55-60° C. for 20 minutes and gradually cooled to 20-25° C. The crystalline compound formed was filtered, washed with methanol (20 ml), dried under reduced pressure for 3 hours to obtain all-trans lycopene (9.86 g) having 86.46% all-E-isomer and 6.62% Z-isomer content.

Examples 2, 3 & 4

Experiments were conducted to demonstrate repeatability of the example 1 as above. The results are tabulated below:

TABLE 4

| | Lycopene | | | Output lycopene | | |
|---|---|---|---|---|---|---|
| Input | all-E (% A) | Z-(% A) | Thiourea input | Yield | all-E (% A) | Z-(% A) |
| 13.1 g | 31.6 | 54.70 | 3.25 g | 11.2 g | 87.4 | 8.8 |
| 13.2 g | 29.7 | 57.9 | 3.25 g | 11.6 g | 83.0 | 14.2 |
| 13.0 g | 40.2 | 46.7 | 3.25 g | 11.3 g | 85.1 | 12.5 |

Example 5

Lycopene having 63.13% of Z-isomer (43 Kg, all E-content: 29.83%) was charged to a reactor containing 2-propanol (260 L). To the resulting suspension, 8 Kg of thiourea was added and heated to maintain 80±2° C. for 15 hrs or until in-process HPLC indicated <15% content of Z-lycopene. The solvent was distilled off at atmospheric pressure followed by distillation at <10 mm Hg. To the resulting mass, methanol (50 L) was added and the mass was distilled at reduced pressure at <55° C. to remove traces of 2-propanol. Methanol (100 L) was added to reactor and the mass was stirred at 55° C. for 15 minutes. The resulting crystalline mass was cooled to 23±2° C., stirred for 1 hr and filtered to recover solid. The wet material was stirred with water (100 L) to remove traces of thiourea, filtered, stirred with methanol (200 L), solid material filtered and dried at 30±2° C. under reduced pressure to obtain 29.2 Kg all-E lycopene (trans) having 84% E-isomer and 9% Z-isomer content.

The procedure of example 5 was repeated with different batches of lycopene with the results obtained as shown in Table 5 below.

TABLE 5

| | Lycopene | | | Output lycopene | | |
|---|---|---|---|---|---|---|
| Input | all-E (% A) | Z-(% A) | Thiourea input | Yield | all-E (% A) | Z-(% A) |
| 43 Kg | 29.83 | 63.13 | 8 Kg | 29.2 Kg | 84 | 9 |
| 43 Kg | 29.67 | 63.09 | 8 Kg | 29.6 Kg | 82 | 10 |
| 43 Kg | 28.2 | 64.16 | 8 Kg | 29.8 Kg | 89 | 7 |
| 43 Kg | 30.76 | 64.21 | 8 Kg | 29.9 Kg | 87 | 7 |

We claim:

1. A process of isomerization of Z-lycopenes in a mixture containing less than 50% of all-E lycopene and more than 50% of the Z-lycopenes, the process comprising adding the Z-lycopenes to a suitable polar solvent medium and then adding thiourea at a temperature of less than 100° C. without pressure to recover an enriched lycopene mixture having an all-E isomer content of greater than 50% (HPLC area %) and a Z-isomer content of less than 50% (HPLC area %).

2. The process as in claim 1, in which thiourea used may be added as a solid or solution or suspension.

3. The process as in claim 1, in which the suitable polar solvent medium used is a $C_1$ to $C_4$ alcohol or mixtures thereof.

4. The process as in claim 1, in which the recovered enriched lycopene mixture has an all-E isomer content of greater than 80% (HPLC area %) and Z-isomer content of less than 20% (HPLC area %).

* * * * *